United States Patent
Keller (10) Patent No.: US 11,627,926 B2
(45) Date of Patent: Apr. 18, 2023

(54) PATIENT COMFORT IN NUCLEAR IMAGING SYSTEM

(71) Applicant: Siemens Medical Solutions USA, Inc., Malvern, PA (US)

(72) Inventor: John Keller, Knoxville, TN (US)

(73) Assignee: Siemens Medical Solutions USA, Inc., Malvern, PA (US)

(*) Notice: Subject to any disclaimer, the term of this patent is extended or adjusted under 35 U.S.C. 154(b) by 435 days.

(21) Appl. No.: 16/948,534

(22) Filed: Sep. 23, 2020

(65) Prior Publication Data

US 2022/0087625 A1 Mar. 24, 2022

(51) Int. Cl.
*A61B 6/00* (2006.01)
(52) U.S. Cl.
CPC .................. *A61B 6/4488* (2013.01)
(58) Field of Classification Search
CPC ... F24F 1/01; F24F 13/26; F24F 7/007; B04C 5/26; B04C 5/28; B04C 5/13; B04C 5/10; B04C 5/185; B04C 5/104; B04C 5/087; B04C 5/16; B04C 5/22; B04C 5/04; B04C 9/00; B04C 2009/004; B04C 2009/001; B04C 2009/002
See application file for complete search history.

(56) References Cited

U.S. PATENT DOCUMENTS

| | | | | |
|---|---|---|---|---|
| 5,800,335 A | * | 9/1998 | Koch | A61B 5/055 600/22 |
| 8,487,618 B2 | * | 7/2013 | Takamori | G01R 33/34007 324/309 |
| 9,335,387 B2 | * | 5/2016 | Chen | G01R 33/28 |
| 2004/0228450 A1 | * | 11/2004 | Mueller | A61B 6/4488 378/199 |
| 2005/0030028 A1 | * | 2/2005 | Clarke | G01R 33/34046 324/318 |
| 2010/0080338 A1 | * | 4/2010 | Fukushima | A61B 6/032 378/4 |
| 2010/0266096 A1 | * | 10/2010 | Sharpless | A61B 6/035 378/4 |
| 2012/0123237 A1 | * | 5/2012 | Canzolino | A61B 6/045 600/407 |
| 2017/0105689 A1 | * | 4/2017 | Hori | A61B 6/035 |
| 2017/0105692 A1 | * | 4/2017 | Sawanobori | A61B 6/4488 |
| 2018/0008219 A1 | * | 1/2018 | Opheij | A61G 13/108 |
| 2018/0133518 A1 | * | 5/2018 | Harper | A61N 5/1049 |
| 2019/0195487 A1 | * | 6/2019 | Bourne | A61B 5/055 |
| 2020/0289074 A1 | * | 9/2020 | Zilberstien | G01T 1/244 |
| 2021/0265120 A1 | * | 8/2021 | Marcotte | G06F 3/0362 |
| 2021/0267683 A1 | * | 9/2021 | Brown | A61B 6/037 |

* cited by examiner

*Primary Examiner* — Dani Fox
*Assistant Examiner* — Soorena Kefayati (57) ABSTRACT

Provided is a novel medical image scanner gantry that includes at least one annular nozzle opening within the patient tunnel where the at least one annular nozzle opening directs a flow of pressurized air toward the back end of the patient tunnel which draws an amount of the ambient air into the patient tunnel to supplement the flow of pressurized air in the patient tunnel to help improve the patient's comfort.

10 Claims, 8 Drawing Sheets

PATIENT COMFORT IN NUCLEAR IMAGING SYSTEM

CROSS-REFERENCE TO RELATED APPLICATIONS

None

FIELD

The present disclosure generally relates to a novel configuration for a medical image scanner gantry that provides cooling and/or warming air flow to the patient for improving the patient comfort.

BACKGROUND

In medical imaging devices such as PET, PET/CT, and MRI scanners, for example, in which the patient is positioned within a tunnel or a bore can present challenging environment for patient comfort. For example, if the room environment is uncomfortably cold or warm to the patient, adjusting the thermostat setting for the room can generally take too long and may not improve the patient's comfort during the scan. Thus, there is a need for a design for a medical image scanning system that can address the patient's comfort needs in terms of the environment temperature moments before or during a scan.

SUMMARY

In one aspect, a medical image scanner gantry, such as for a PET scanner, PET/CT scanner, a MRI scanner, etc., configured for providing cooling or warming air to the patient located inside the patient tunnel of the medical image scanner to improve the patient comfort during a scan procedure is disclosed. Such improved medical image scanner gantry comprises a scanner housing having an annular structure that defines a patient tunnel and a front funnel portion of the patient tunnel. The medical image scanner gantry also comprises an air plenum portion comprising an annular space inside the scanner housing for carrying a flow of pressurized air when the medical image scanner is in operation; wherein the patient tunnel portion comprises an opening at its front end and an opening at its back end and defines a bore extending between the two openings; wherein the front funnel portion forming the opening at the front end of the patient tunnel portion; and at least one annular nozzle opening configured to direct a flow of a portion of the pressurized air out of the air plenum portion and toward the back end of the patient tunnel; whereby when the flow of a portion of the pressurized air flows out of the at least one annular nozzle opening toward the back end of the patient tunnel, an amount of ambient air is drawn into the patient tunnel and joins the flow of pressurized air flowing out of the annular nozzle opening and flow toward the back end of the patient tunnel.

In some embodiments, a novel medical image scanner gantry comprises: a scanner housing having an annular structure that defines a patient tunnel and a front funnel portion of the patient tunnel, wherein the patient tunnel portion comprises an opening at its front end and an opening at its back end and defines a bore extending between the two openings, wherein the front funnel portion forming the opening at the front end of the patient tunnel portion; wherein the scanner housing comprising: a plurality of detector electronic assemblies positioned within the scanner housing; and an air plenum portion comprising: an annular space inside the scanner housing for carrying a flow of pressurized air when the medical image scanner is in operation; a first annular nozzle opening configured to direct a flow of a portion of the pressurized air out of the air plenum portion and toward the detector electronic assemblies; and an annular interior wall that defines an entry opening of the patient tunnel portion near the front end of the patient tunnel portion; at least one second annular nozzle opening defined between the annular interior wall and the scanner housing, wherein the at least one second annular nozzle opening is configured to direct a flow of a portion of the pressurized air exiting the first annular nozzle opening toward the back end of the patient tunnel, whereby the flow of pressurized air exiting the at least one second annular nozzle opening toward the back end of the patient tunnel draws an amount of ambient air into the patient tunnel and supplements the flow of air in the patient tunnel.

Medical image scanner systems fitted with one of the novel medical image scanner gantries are also disclosed.

BRIEF DESCRIPTION OF THE DRAWINGS

The features of the embodiments described herein will be more fully disclosed in the following detailed description, which is to be considered together with the accompanying drawings wherein like numbers refer to like parts. All drawing figures are schematic and they are not intended to represent actual dimensions of the structures or relative ratios of their dimensions.

DETAILED DESCRIPTION

This description of the exemplary embodiments is intended to be read in connection with the accompanying drawings, which are to be considered part of the entire written description. The drawing figures are not necessarily to scale and certain features may be shown exaggerated in scale or in somewhat schematic form in the interest of clarity and conciseness. In the description, relative terms such as "horizontal," "vertical," "up," "down," "top" and "bottom" as well as derivatives thereof (e.g., "horizontally," "downwardly," "upwardly," etc.) should be construed to refer to the orientation as then described or as shown in the drawing figure under discussion. These relative terms are for convenience of description and normally are not intended to require a particular orientation. Terms including "inwardly" versus "outwardly," "longitudinal" versus "lateral" and the like are to be interpreted relative to one another or relative to an axis of elongation, or an axis or center of rotation, as appropriate. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise. The term "operatively connected" is such an attachment, coupling or connection that allows the pertinent structures to operate as intended by virtue of that relationship.

Referring to FIGS. 1-4, provided herein is an example of a novel configuration for a medical image scanner gantry 100 that is configured to provide cooling or warming air flow into the bore of the patient tunnel of the scanner gantry to improve the patient comfort. In some embodiments, the medical image scanner gantry 100 comprises a scanner housing 130 having an annular structure that form a patient tunnel 110 and a front funnel portion 120 of the patient tunnel.

The patient tunnel 110 comprises an opening at its front end 111 and an opening at its back end 112 and defines a bore 115 between the two openings. The designation of "front" in referring to the front end 111 refers to the end of the patient tunnel bore 115 where the patient's body enters for the scanning operation. The bore 115 is the interior space of the patient tunnel 110 in which a patient resides during a scanning operation. The front funnel portion 120 forms the opening at the front end 111 of the patient tunnel 110.

The scanner housing 130 also comprises an air plenum portion 135 and at least one annular nozzle opening 137. The air plenum portion 135 comprises an annular interior space 135' for carrying a flow of pressurized air when the medical image scanner is in operation. The annular interior space 135' in some embodiments can also be described as having a substantially toroid shape.

The at least one annular nozzle opening 137 is configured for directing a localized high velocity flow H of a portion of the pressurized air out of the air plenum portion and toward the back end 112 of the patient tunnel. When the flow H of pressurized air flows out of the at least one annular nozzle opening 137 toward the back end 112 of the patient tunnel 110, an amount of ambient air is drawn into the patient tunnel and joins the flow of pressurized air flowing out of the annular nozzle opening and flow toward the back end 112 of the patient tunnel 110. This air flow through bore 115 of the patient tunnel 110 can improve the comfort level of a patient positioned in the bore 115 during a scanning operation.

The supplementing ambient air is drawn into the bore 115 by inertance effect. When the localized high velocity flow H of air flows out of the at least one annular nozzle opening 137 toward the back end 112 of the patient tunnel 110, a lower pressure zone is created behind the flow H of the high velocity air, i.e. in the region between the nozzle opening 137 and the front end 111 of the patient tunnel 110. This lower pressure zone draws an amount of the ambient air in the vicinity of the funnel portion 120 and near the front end 111 of the patient tunnel 110 into the bore 115 of the patient tunnel 110 which joins the high velocity flow H of pressurized air flowing out of the at least one annular nozzle opening 137.

This flow of air in the bore 115 of the patient tunnel 110 provides air flow around a patient positioned in the bore 115 during a scanning session and enhance the comfort level of the patient. If the patient feels uncomfortably warm in the scanner room, this flow of air within the patient tunnel 110 can provide cooling effect for the patient during the scanning session. If the patient feels uncomfortably cold in the scanner room, this flow of air within the patient tunnel 110 can be warmed by warming the pressurized air exiting the nozzle opening 137. In the case of warming a patient who feels cold, the flow rate of the warmed air exiting the high pressure nozzle is desirably relatively low as to minimize the volume of air that is pulled into the bore 115. This warming of the air exiting the at least one high-pressure annular nozzle opening 137 can be accomplished using electric heating elements provided along the at least one annular nozzle opening 137. In some embodiments, the waste heat from the air cooled electronics in the scanner housing 130 could also be the source of heat used to raise the air temperature.

Figure 4:
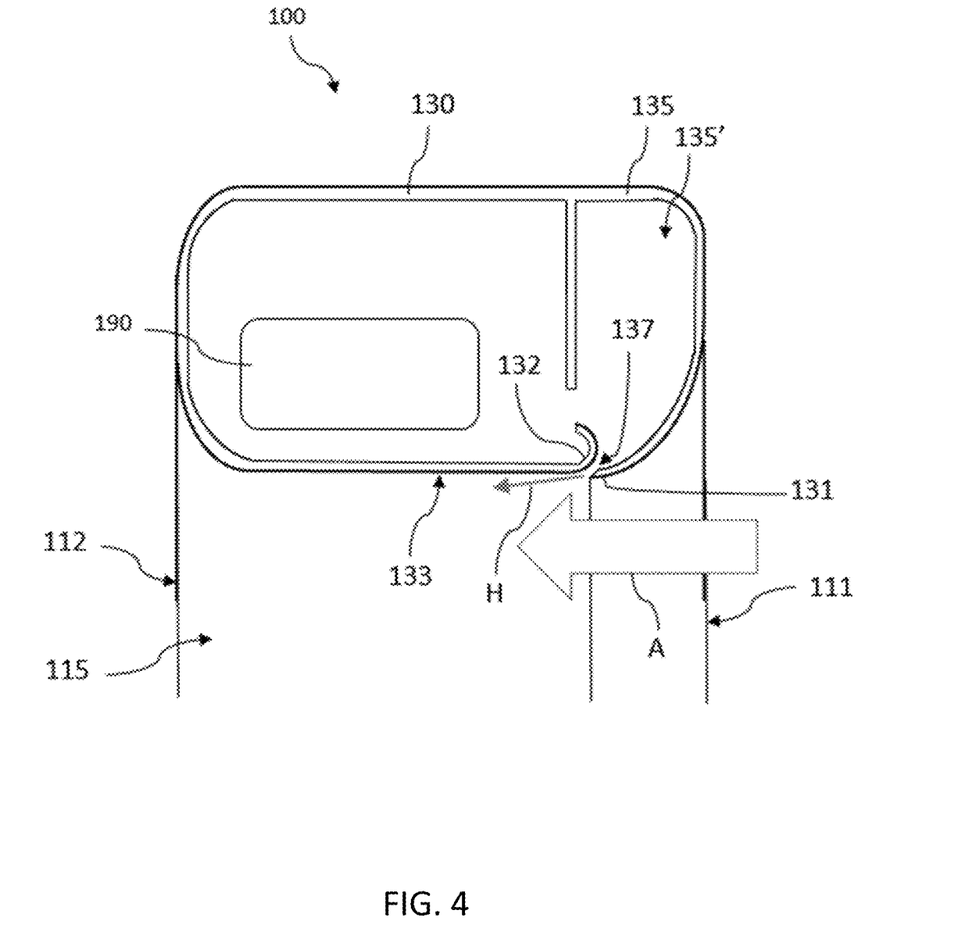
FIG. 4 is a detailed longitudinal sectional view illustration of a portion of the improved medical image scanner gantry shown in FIGS. 1-3.

Referring to the detailed sectional view illustrated in FIG. 4, the at least one annular nozzle opening 137 is formed by a discontinuity in the plenum portion 135 of the scanner housing 130 that directs the flow H of the high velocity air toward the back end 112 of the patient tunnel 110. The scanner housing's wall has two annular edges 131 and 132 between the funnel portion 120 and the patient tunnel 110 wall that form the at least one annular nozzle opening 137. The first edge 131 is closer to the front end 111 of the patient tunnel 110 and the second edge 132 is closer to the back end 112 of the patient tunnel 110.

Figure 1:
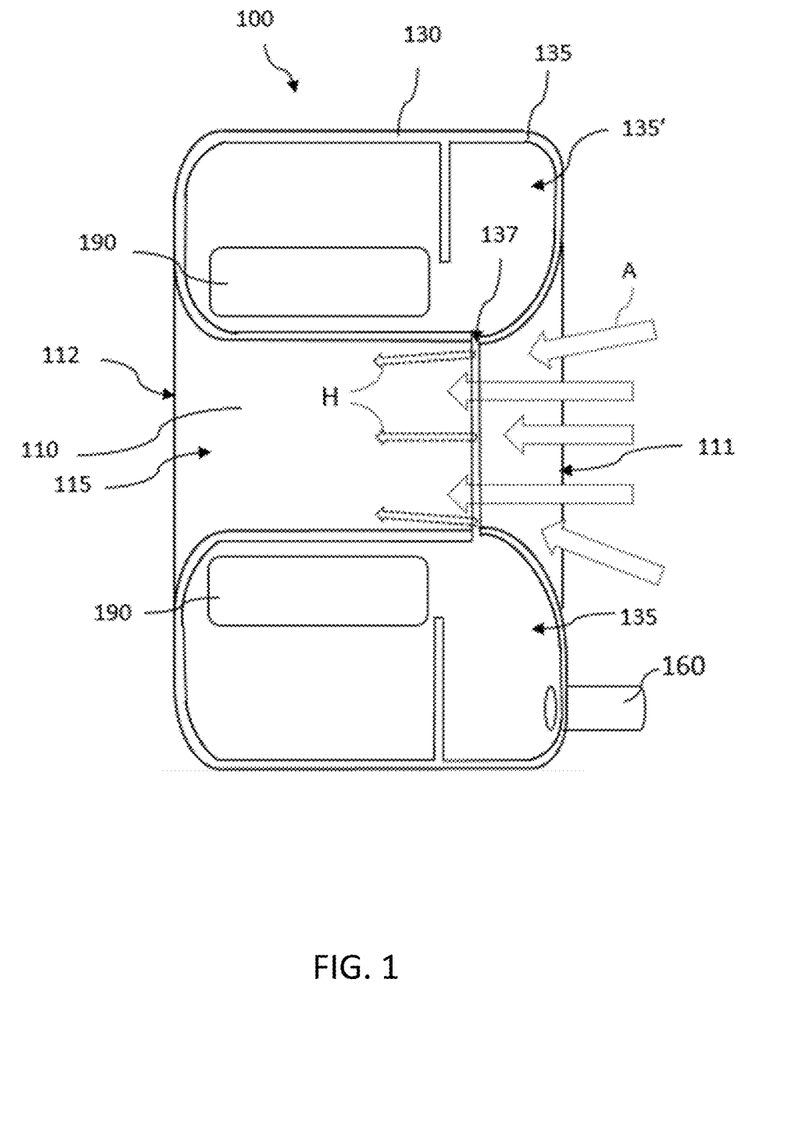
FIGS. 1-3 are longitudinal (with respect to the longitudinal axis L of the bore 115) sectional view illustrations of an example of an improved medical image scanner gantry according to the present disclosure.
Figure 2:
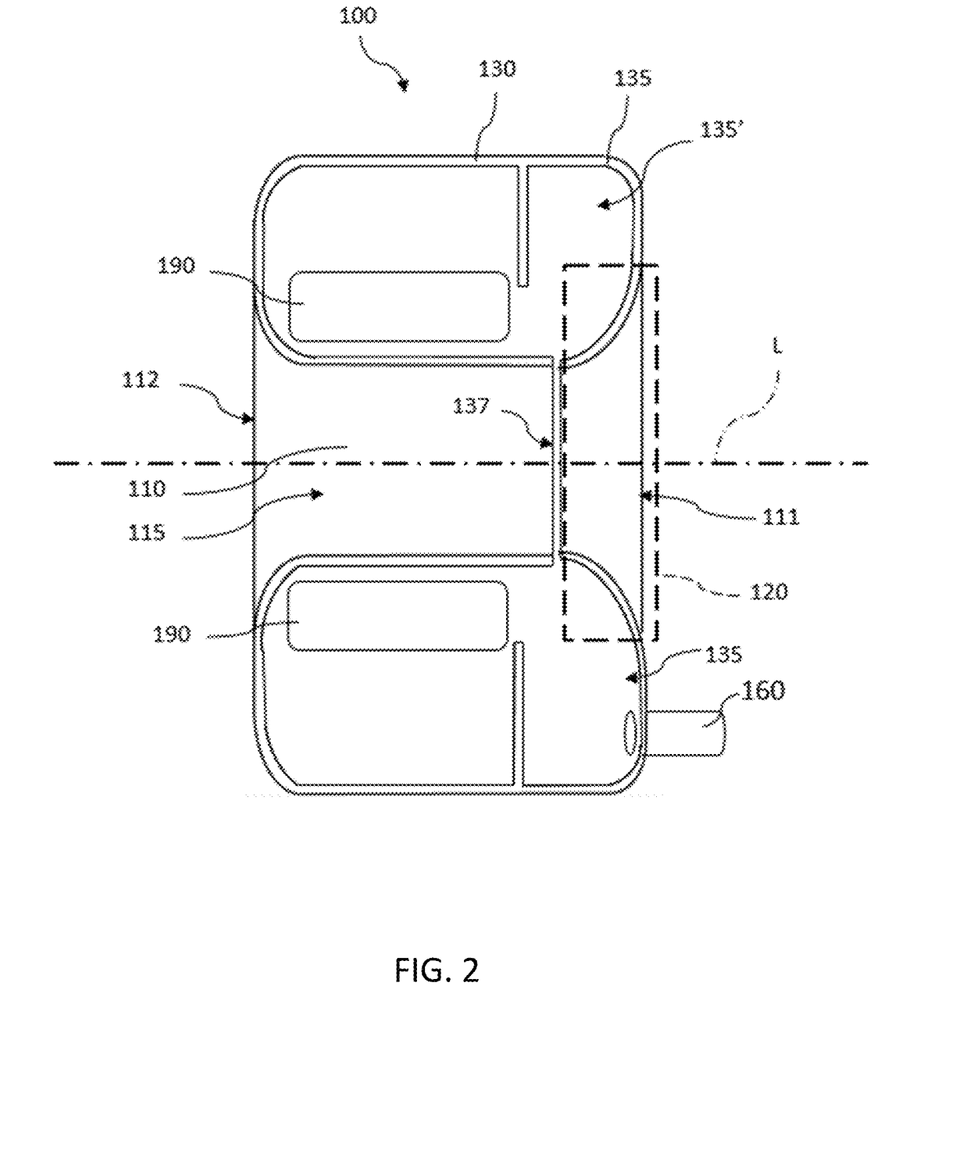
Figure 3:
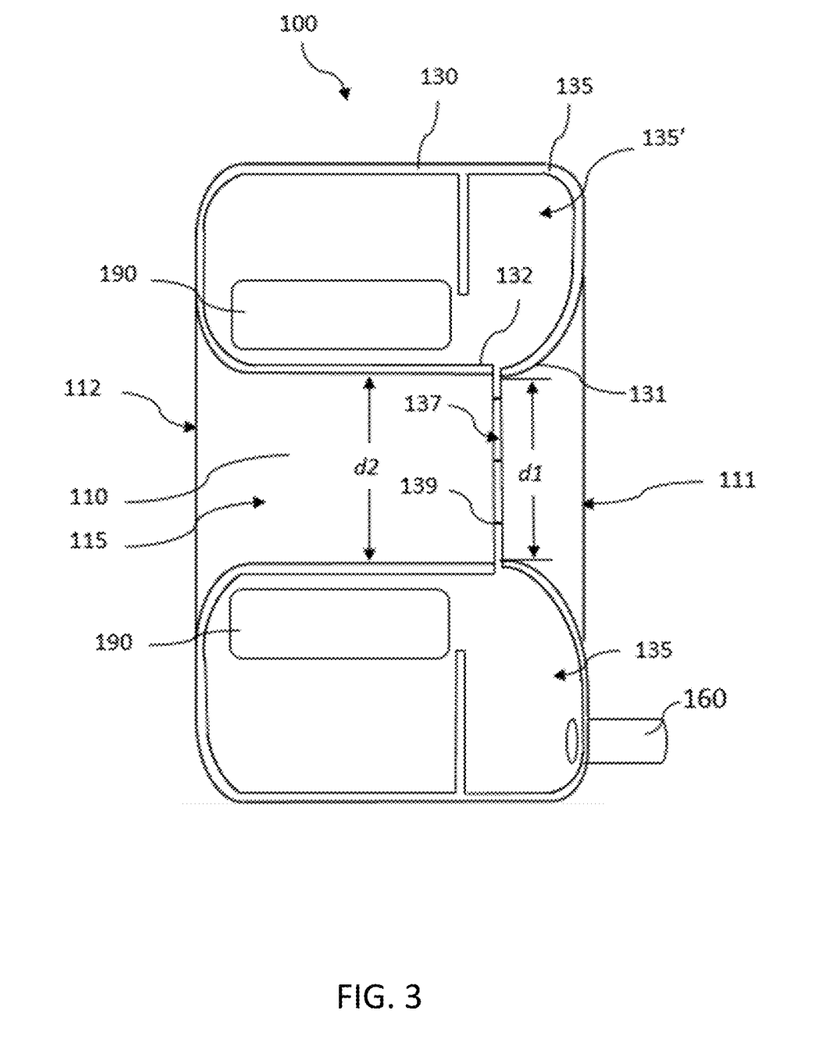

Referring to FIG. 3, the first edge 131 and the second edge 132 circumscribe the bore 115 formed by the patient tunnel 110. The first edge 131 forms an opening that has a diameter d1 that is smaller than the diameter d2 of the opening formed by the second edge 132. Thus, the at least one nozzle opening 137 is formed by the gap between the first edge 131 and the second edge 132. The at least one nozzle opening 137 formed between the first edge 131 and the second edge 132 face toward the back end 112 of the patient tunnel 110. This configuration of the first and second edges 131, 132 allows the high velocity air flow H exiting the plenum portion 135 via the at least one nozzle opening 137 to be directed toward the back end 112 of the patient tunnel 110.

Figure 7:
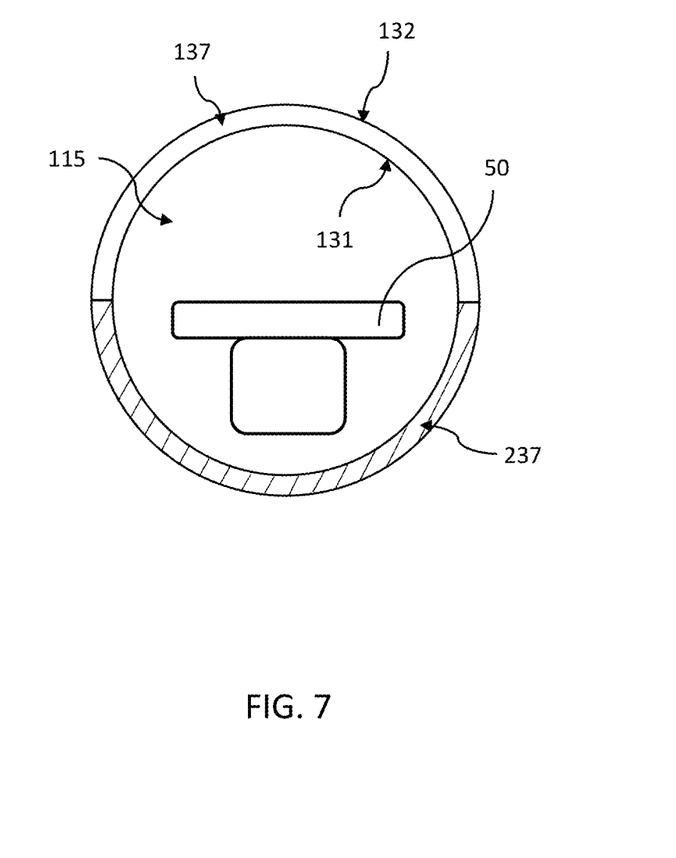
FIG. 7 is a cross-sectional view (orthogonal to the longitudinal axis L of the bore 115) illustration showing the annular nozzle opening of the present disclosure.

In some embodiments, the annular nozzle opening 137 may not necessarily span the full 360-degrees of the circumference of the patient tunnel 110. The gap between the first edge 131 and the second edge 132 can be configured to be blocked in some sections along the circumference of the patient tunnel 110 so that the annular nozzle opening 137 is provided only in certain sections or segments along the circumference of the patient tunnel 110. For example, in many PET scanner systems, it may not be necessary to provide a flow of air underneath the patient bed. Thus, in some embodiments, the annular nozzle opening 137 can only be present in the segment along the circumference of the patent tunnel 110 that encircles the portion of the patient tunnel 110 that is above the patient bed 50. This is schematically illustrated in FIG. 7. FIG. 7 is a schematic view into the bore 115 from the back end 112 of the patient tunnel 110 toward the front end 111. The annular nozzle opening 137 is formed by the gap between the first edge 131 and the second edge 132. In this illustrated example, the annular nozzle opening 137 does not extend below the patient bed 50. The portion 237 of the gap between the first edge 131 and the second edge 132 shown with a cross-hatch is configured to be blocked so that the pressurized air from the plenum portion 135 does not flow out into the portion of the bore 115 below the patient bed 50. The annular nozzle opening 137 can be configured to have a variety of different length along the circumference of the patient tunnel 110.

Figure 8:
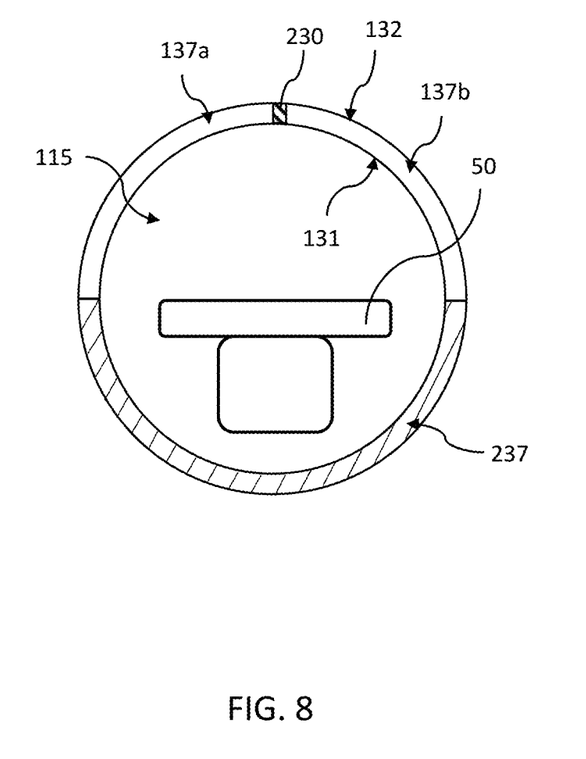
FIG. 8 is a cross-sectional view (orthogonal to the longitudinal axis L of the bore 115) illustration showing another embodiment for a configuration of the annular nozzle opening of the present disclosure.

In some embodiments, the gap formed between the first edge 131 and the second edge 132 can be configured to have more than one annular nozzle opening 137. An example of such embodiment is illustrated in FIG. 8. In FIG. 8, the gap between the first edge 131 and the second edge 132 is divided into two segments by a divider 230 and effectively two annular nozzle openings 137a and 137b are provided. The scanner gantry 100 can be configured to segment the gap between the first edge 131 and the second edge 132 into any desired number of annular nozzle openings. The medical scanner gantry 100 can comprise at least one annular nozzle opening 137. This variation of providing at least one annular nozzle opening can be applied to the embodiment of the medial scanner gantry 100' shown in FIGS. 5-6. In the medical scanner gantry 100', the concept of providing at least one annular nozzle opening can be applied to both the first annular nozzle opening 138 and the second annular nozzle opening 137.

The flow of pressurized air inside the plenum portion 135 is provided when the medical image scanner is operational for cooling the electronic components 190 of the scanner that are usually contained inside the scanner housing 130 of the scanner gantry 100. In PET and PET/CT scanners, for example, a plurality of PET detector electronic assemblies 190 can be provided as part of or connected to the scanner gantry 100 and are located inside the gantry housing 130 at locations that are in fluid communication with the interior annular space 135' of the air plenum 135 so that the pressurized air flowing through the plenum 135 can be directed to the detector electronic assemblies 190 for cooling when the medical image scanner is in operation.

In some embodiments, a plurality of fins 139 (shown in FIG. 3) can be provided bridging the first and second edges 131, 132 and maintaining a desired spacing between the first and second edges. The plurality of fins 139 can be positioned at designated points along the circumference of the first and second edges 131, 132 at regular interval. The fins 139 are preferably not too thick and are oriented substantially in radial direction (i.e. in-plane with the longitudinal axis L of the bore 115 (see FIG. 2)) so that the fins do not substantially interfere with the flow H of air exiting the annular nozzle opening 137.

In some embodiments, the air plenum 135 comprises an air inlet 160 for receiving the flow of pressurized air from a remote source (not shown).

According to another aspect, a medical image scanner system is disclosed. The medical image scanner system comprises the medical image scanner gantry 100 described herein.

Figure 5:
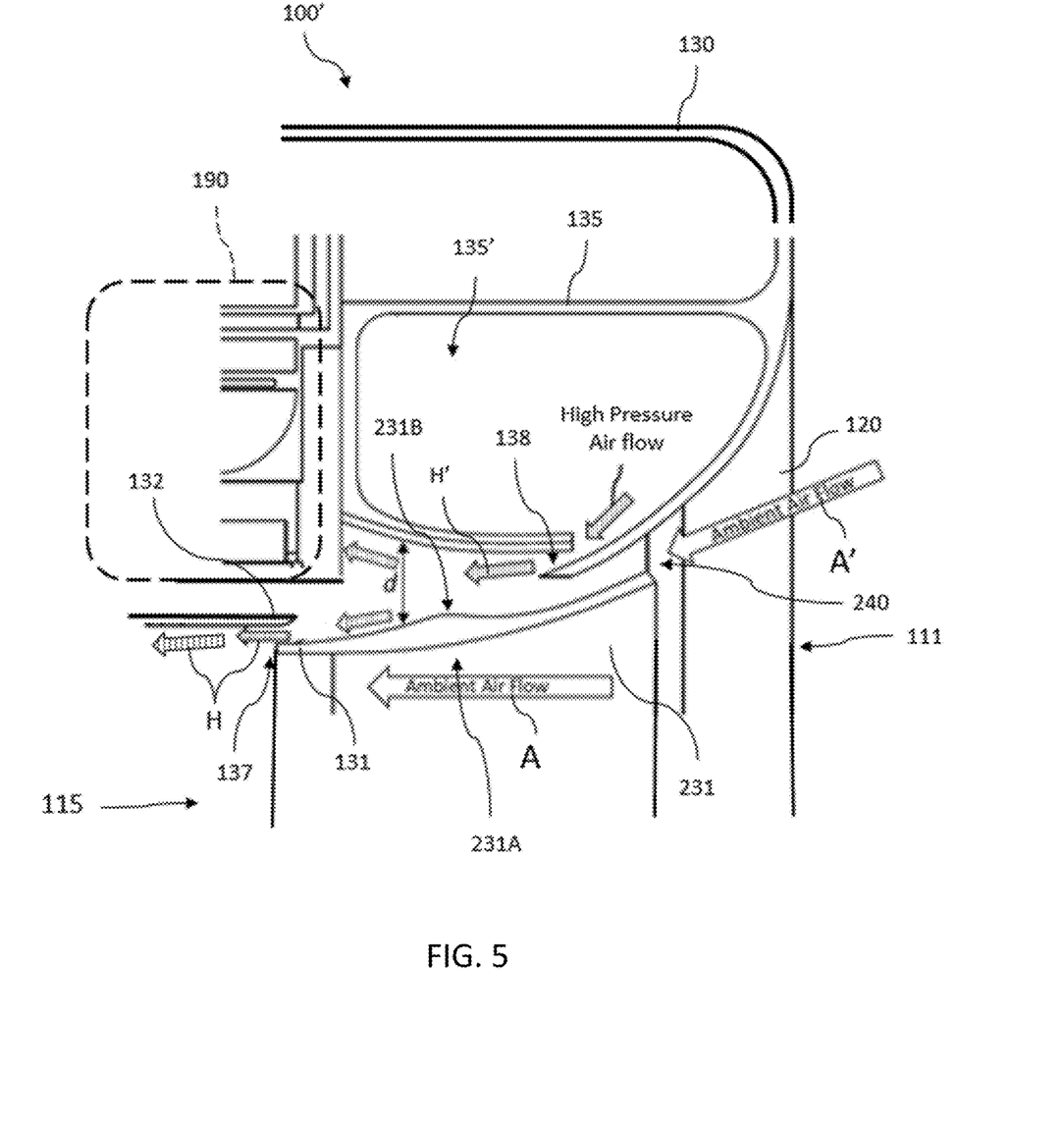
FIG. 5 is a detailed longitudinal sectional view illustration of a portion of another example of the improved medical image scanner gantry according to the present disclosure.
Figure 6:
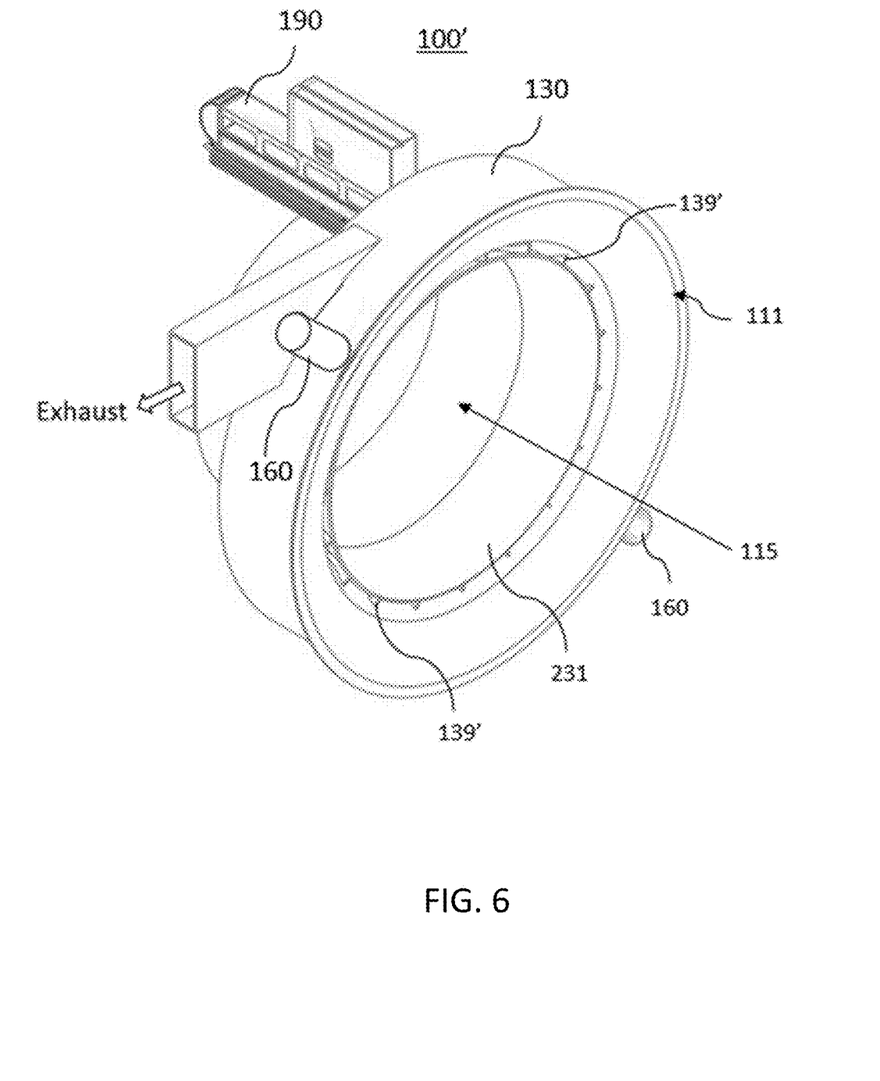
FIG. 6 is an isometric view illustration of a medical image scanning gantry of FIG. 5.

Referring to FIG. 5, another example of a novel configuration for a medical image scanner gantry 100' that is configured to provide cooling or warming air flow into the bore 115 of the patient tunnel of the scanner gantry to improve the patient comfort is disclosed. In this example, the scanner housing 130 is configured to provide the patient comforting air flow into the bore 115 supplemented by ambient air using the inertance principle as mentioned above and also provide cooling air to the detector electronic assembly 190 that is also supplemented by ambient air using the inertance principle.

As in the other embodiments discussed above, the annular interior space 135' of the air plenum portion 135 in this embodiment also carries a flow of pressurized air when the medical image scanner is in operation. The air plenum portion 135 comprises at least one first annular nozzle opening 138 that is configured to direct a localized high velocity flow H' of pressurized air from the annular interior space 135' toward the back end 112. This flow H' of pressurized air travels with sufficient velocity so that it creates a lower pressure zone behind the flow H' of the pressurized air, i.e. in the region between the first annular nozzle opening 138 and the front end 111 of the patient tunnel 110. This low pressure zone draws an amount of the ambient air A' in the vicinity of the funnel portion 120 and near the front end 111 of the patient tunnel 110 into the patient tunnel 110 which joins the high velocity flow H' of pressurized air flowing out of the first annular nozzle opening 138. The supplemented high velocity flow H' of air flows toward the detector electronic assembly 190 and provide cooling for the detector electronic assembly 190.

Additionally, this embodiment also comprises an annular interior wall 231 that defines the entry opening of the patient tunnel portion 110 near the front end 111 and also defines at least one second annular nozzle opening 137. The second annular nozzle opening 137 is configured for directing a localized high velocity flow H, of a portion of the supplemented high velocity flow H' described above, toward the back end 112 of the patient tunnel 110. The second annular nozzle opening 137 is formed by two annular edges 131 and 132. The first edge 131 provided by the annular interior wall 231. The second annular edge 132 is provided by a portion of the scanner housing 130.

As shown in FIG. 5, as the supplemented high velocity flow H' of air flows toward the detector electronic assembly 190, a portion of the supplemented high velocity flow H' gets diverted through the second annular nozzle opening 137 and exits the second annular nozzle opening 137 as the high velocity flow H.

When the high velocity flow H of pressurized air flows out of the second annular nozzle opening 137 toward the back end 112 of the patient tunnel 110, the high velocity flow H of air travels with sufficient velocity so that it creates a lower pressure zone behind the flow H of air, i.e. in the region between the second annular nozzle opening 137 and the front end 111 of the patient tunnel 110. This lower pressure zone draws an amount of the ambient air A in the vicinity of the funnel portion 120 and near the front end 111 of the patient tunnel 110 into the patient tunnel 110 which joins the high velocity flow H of pressurized air flowing out of the second annular nozzle opening 137. This air flow through the patient tunnel 110 can improve the comfort level of a patient positioned inside the patient tunnel 110 during a scanning operation.

The annular interior wall 231 is nested inside the annular structure of the air plenum 135, whereby a supplemental air inlet 240 is formed between the annular interior wall 231 and the air plenum 135. The amount of the ambient air A' from the vicinity of the funnel portion 120 that is drawn in by the high velocity flow H' of pressurized air exiting the first annular nozzle opening 138 gets drawn in through the supplemental air inlet 240.

The annular interior wall 231 nested inside the annular structure of the air plenum 135 and is spaced apart from the air plenum 135. The annular interior wall 231 is preferably configured to maintain a distance d from the air plenum 135 structure so that the supplemental air inlet 240 and the second annular nozzle opening 137 can be maintained.

In some embodiments, a plurality of fins 139' are provided between the annular interior wall 231 and the air plenum 135 structure to attach the annular interior wall 231 to the air plenum 135 structure and to maintain the spacing between the annular interior wall 231 and the air plenum 135. The plurality of fins 139' can be positioned at designated points along the circumference of the annular interior wall 231 at regular interval. The plurality of fins 139' are radially oriented with respect to the longitudinal axis L of the bore 115 of the patient tunnel portion 110 so that each of the fins 139' is in-plane with the longitudinal axis L. This configuration minimizes any interference to the air flow between the annular interior wall 231 and the air plenum 135 presented by the fins 139'. The configuration also helps minimize any interference the fins 139' may present to the flow H of air through the second annular nozzle opening 137.

The annular interior wall 231 comprises a first annular surface 231A facing the bore 115 defined by the patient tunnel portion 110 and a second annular surface 231B facing the air plenum.

It will be understood that the foregoing description is of exemplary embodiments of this invention, and that the invention is not limited to the specific forms shown. Modifications may be made in the design and arrangement of the elements without departing from the scope of the invention.

I claim:

1. A medical image scanner system comprising:
   a medical image scanner gantry comprising:
      a scanner housing having an annular structure that defines a patient tunnel portion and a front funnel portion of the patient tunnel, and comprising:
         an air plenum portion comprising an annular space inside the scanner housing for carrying a flow of pressurized air when the medical image scanner is in operation;
         wherein the patient tunnel portion comprises an opening at a front end of the patient tunnel portion and an opening at a back end of the patient tunnel portion, wherein the patient tunnel portion defines a bore extending between the two openings at the front end and the back end of the patient tunnel portion;
         wherein the front funnel portion forming the opening at the front end of the patient tunnel portion; and
         at least one annular nozzle opening configured to direct a flow of a portion of the pressurized air out of the air plenum portion and toward the back end of the patient tunnel;
      whereby when the flow of a portion of the pressurized air flows out of the at least one annular nozzle opening toward the back end of the patient tunnel, an amount of ambient air is drawn into the patient tunnel and joins the flow of pressurized air flowing out of the at least one annular nozzle opening and flow toward the back end of the patient tunnel.

2. The medical image scanner system of claim 1, wherein the at least one annular nozzle opening is formed by a first edge and a second edge, wherein the first edge and the second edge circumscribe the bore formed by the patient tunnel.

3. The medical image scanner system of claim 1, wherein the air plenum comprises an air inlet for receiving the flow of pressurized air from a remote source.

4. The medical image scanner system of claim 2, wherein the first edge has a smaller diameter than the second edge, whereby the at least one annular nozzle opening formed between the first edge and the second edge faces toward the back end of the patient tunnel and allows the flow of air exiting the annular nozzle opening to be directed toward the back end of the patient tunnel.

5. The medical image scanner system of claim 2, wherein a plurality of fins are provided bridging the first edge and the second edge maintaining a desired spacing between the first edge and the second edge.

6. A medical image scanner system comprising:
   a medical image scanner gantry comprising:
      a scanner housing having an annular structure that defines a patient tunnel portion and a front funnel portion of the patient tunnel, wherein the patient tunnel portion comprises an opening at a front end of the patient tunnel portion and an opening at a back end of the patient tunnel portion, wherein the patient tunnel portion defines a bore extending between the two openings at the front end and the back end of the patient tunnel portion, wherein the front funnel portion forming the opening at the front end of the patient tunnel portion;
      wherein the scanner housing comprising:
         a plurality of detector electronic assemblies positioned within the scanner housing; and
         an air plenum portion comprising:
            an annular space inside the scanner housing for carrying a flow of pressurized air when the medical image scanner is in operation;
            at least one first annular nozzle opening configured to direct a flow of a portion of the pressurized air out of the air plenum portion and toward the detector electronic assemblies; and
      an annular interior wall that defines an entry opening of the patient tunnel portion near the front end of the patient tunnel portion; and
      at least one second annular nozzle opening defined between the annular interior wall and the scanner housing, wherein the at least one second annular nozzle opening is configured to direct a flow of a portion of the pressurized air exiting the first annular nozzle opening toward the back end of the patient tunnel,
      whereby the flow of pressurized air exiting the at least one second annular nozzle opening toward the back end of the patient tunnel draws an amount of ambient air into the patient tunnel and supplements the flow of air in the patient tunnel.

7. The medical image scanner system of claim 6, wherein the at least one second annular nozzle opening is formed by a first edge and a second edge, wherein the first edge and the second edge circumscribe the bore formed by the patient tunnel.

8. The medical image scanner system of claim 6, wherein the air plenum comprises an air inlet for receiving the flow of pressurized air from a remote source.

9. The medical image scanner system of claim 7, wherein the first edge has a smaller diameter than the second edge, whereby the at least one second annular nozzle opening formed between the first edge and the second edge faces toward the back end of the patient tunnel and allows the flow of air exiting the at least one second annular nozzle opening to be directed toward the back end of the patient tunnel.

10. The medical image scanner system of claim 7, wherein a plurality of fins are provided bridging the annular interior wall and the air plenum and maintaining a desired spacing between the annular interior wall and the air plenum.

* * * * *